United States Patent
Martin et al.

(10) Patent No.: US 6,815,213 B1
(45) Date of Patent: Nov. 9, 2004

(54) METHOD FOR ANALYZING A SAMPLE OF A COMPLEX MOLECULE RELATIVELY TO A REFERENCE BATCH OF THE SAME COMPLEX MOLECULE

(75) Inventors: Gerard Martin, Nantes (FR); Gilles Martin, Nuremberg (DE)

(73) Assignee: Eurofins Scientific, Nantes Cedex (FR)

( * ) Notice: Subject to any disclaimer, the term of this patent is extended or adjusted under 35 U.S.C. 154(b) by 206 days.

(21) Appl. No.: 10/019,000

(22) PCT Filed: Jun. 21, 2000

(86) PCT No.: PCT/FR00/01712

§ 371 (c)(1),
(2), (4) Date: Apr. 22, 2002

(87) PCT Pub. No.: WO00/79569

PCT Pub. Date: Dec. 28, 2000

(30) Foreign Application Priority Data

Jun. 22, 1999 (FR) .............................. 99 07943

(51) Int. Cl.⁷ .............................. G01N 24/00
(52) U.S. Cl. .................... 436/173; 436/174; 436/2; 436/86; 436/94; 436/95
(58) Field of Search .............................. 436/173, 174, 436/2, 86, 94, 95

(56) References Cited

FOREIGN PATENT DOCUMENTS

| EP | 0 567 276 | 11/1993 |
|---|---|---|
| FR | 2 673 291 | 8/1992 |
| GB | 2 120 007 | 11/1983 |

OTHER PUBLICATIONS

Martin et al. "A new method for the identification of the origin of natural products. Quantitative deuterium NMR at the natural abundance level applied to the characterization of anetholes", J. Am. Chem. Soc., (1982), 104(9), 2658–9.*

Caer et al. "Determination of site–specific carbon isotope ratios at natural abundance by carbon–13 nuclear magnetic resonance spectroscopy", Analytical Chemistry (1991), 63(20), 2306–13.*

Vallet et al. "Combination of mass spectrometry and site–specific NMR isotope analyses in the characterization of amino acids" Journal of Agricultural and Food Chemistry (1992), 40(1), 81–7.*

Hanneguelle et al. "Authentication of essential oils containing linalool and linalyl acetate by isotopic methods", Journal of Agricultural and Food Chemistry (1992), 40(1), 81–7.*

Martin et al. "Application of 2H SNIF–NMR and 13C SIRA–MS Analyses to Maple Syrup: Detection of Added Sugars" J. Agric. Food Chem. (1996), 44(10), 3206–3213.*

Jamin et al. "Multi–element and multi–site isotopic analysis of nicotine from tobacco leaves", Plant, Cell and Environment (1997 20, pp. 589–599.*

* cited by examiner

*Primary Examiner*—Yelena G. Gakh
(74) *Attorney, Agent, or Firm*—Young & Thompson

(57) ABSTRACT

The invention concerns a method for analyzing a sample of a complex molecule relatively to a reference batch of the same complex molecule. Said method is characterized in that it consists in breaking up the complex molecule into at least two molecular sub-entities; in determining, on the basis of the atomic sites of said products of the breakup involved in the breakup reactions, the isotope(s) to be analyzed; and in establishing, for at least part of the breakup products, their isotopic profile; and in comparing the isotopic profile of the products of the breakup with the isotopic profile of the raw material(s) previously indexed and/or with the isotopic profile of the reference complex molecule subjected to the same breakup reactions. The invention is useful for detecting counterfeiting in manufacturing processes.

5 Claims, No Drawings

METHOD FOR ANALYZING A SAMPLE OF A COMPLEX MOLECULE RELATIVELY TO A REFERENCE BATCH OF THE SAME COMPLEX MOLECULE

The present invention relates to a process for the analysis of a sample of a complex molecule relative to a reference batch of the same complex molecule, so as particularly to determine their degree of similarity and/or the characterization of their process of production.

Counterfeiting complex products has become a veritable scourge, in particular in the fine chemical, cosmetic and pharmaceutical industries. The detection of counterfeiting of complex products by physico-chemical analysis is often based on the analysis of traces of secondary products of the synthesis, of catalysts or impurities. For example, it has been determined by chromatographic analysis in liquid phase (Asakawa, Shuichi; Kato, Koichi; Inoma, SusumuHakodate Customs Laboratory, Hakodate-shi, 040, Japan, Kanzei Chuo Bunsekishoho (1997), 36, 37–43) that certain glyphosphate base herbicides, produced in the United States and imported into Japan, infringe Japanese patents. By also using a gas phase chromatographic technique coupled with mass spectrometry, E. Charton, M. Wierer, J. M. Spieser, A. Van Dorsselaer, and G. Rautmann (European Department for the Quality of Medicines, Council of Europe, Strasbourg, F-67029, Pharm. Pharmacol. Commun. (1999), 5(1), 61–66) have been able to detect a counterfeit of a medication, somatropine, described in the European pharmacopea, which was in fact a product derived from somatropine of human origin. Conventional chemical methods have permitted proving that tablets of a narcotic substance, fenethylline, were prepared by copying a German patent (N. Al-Gharably and A. R. Al-Obaid, College of Pharmacy, Kind Saud University, Riyadh, 11451, Saudi Arabia, J. Forensic Sci. Soc. (1994), 34(3), 165–7). Similarly, counterfeiting of antibiotics of the β-lactam series have been studied by capillary electrophoresis, at the "National Forensic Chemistry Center" of the "U.S. Food and Drug Administration", 1141 Central Parkway, Cincinnati, Ohio, 45202, USA and described in the Journal of Chromatography, A (1994), 674(1–2), 153–63.

These compositional methods are not always effective and they can lead to false positives. Moreover, they cannot be used in all cases because of the absence of characteristic tracers.

Another process for the authentication of the origin of a product constituted by a mixture of organic compounds, is described in French patent 2.673.291. This process comprises a separative analysis step for the product by gas phase chromatography, a step of transformation to $CO_2$ by combustion of the compounds of the product, followed by a step of analysis by isotopic mass spectrometry so as to measure the enrichment in $C_{13}$ of each compound of the mixture before choosing a compound to mark, particularly by modifying the enrichment in $C_{13}$ of this compound or by adding similar molecules whose richness in $C_{13}$ has first been increased or decreased. Enrichment by isotopic marking necessary for the authentication of the origin of a product is a major drawback of this process. Thus, this step requires the manufacturer to modify his industrial process to be able to mark and authenticate his products. This requirement is connected to the series of steps used in the analysis process, these steps being unable to obtain sufficiently detailed information as to the origin of the products to avoid a marking step of the product by enrichment.

There is also known, as is described in British Patent 2120007, an analysis process consisting in fragmenting a molecule by means of an electron beam in a mass spectrometer chamber with double focusing to obtain metastable ions analyzable by means of said mass spectrometer. However, in this process, the step of fragmentation does not permit obtaining molecular sub-entities, products perfectly stable and isolable, but rather metastable ions of a lifetime of the order of several fractions of a second. Moreover, the nature of the fragments as well as the molecular site where the cleavage is carried out by the electron beam of the mass spectrometer, are conditioned by the presence of the isotope to be determined. These two characteristics of this process distinguish it fundamentally from a process in which a mass spectrometer is used for the isotopic ratios.

Correspondingly, more powerful analytic techniques have been developed. Such is the case of the mass spectrometry of isotopic ratios (MSIR). Thus, it is possible to characterize the natural specific isotopic fractionation by Nuclear Magnetic Resonance Specific Natural Isotope Fractionation (NMR-SNIF method) by measuring the isotopic contents at several molecular sites (or even al the sites) of a molecule. However, this technique is at present used only for simple molecules that can be directly analyzed.

An object of the present invention is to provide a process for the analysis of complex molecules based on an original methodology using isotopic techniques in natural abundance.

Another object of the present invention is to provide a process for the analysis of complex molecules permitting differentiating a batch of complex molecules relative to another batch and establishing a posteriori the history of the process of production of such a complex molecule without having first modified the process for production of such a complex molecule.

To this end, the invention has for its object a process for the analysis of a sample of a complex molecule relative to a reference batch of the same complex molecule so as particularly to determine their degree of similarity and/or the characterization of their process of production, characterized in that the complex molecule is cleaved into at least two molecular sub-entities, in that, if necessary, at least one of the cleavage products is cleaved into at least two new molecular sub-entities and in that this cleavage operation is repeated on at least a portion of the cleavage products until there are obtained analyzable and isolable molecular sub-entities, and in that there is determined, as a function of the atomic sites of the cleavage products in question, by generally chemical cleavage reactions, the isotope or isotopes to be studied, in that there is established, for at least one portion of the cleavage products, their isotopic profile and in that the isotopic profile of the cleavage products is compared to the isotopic profile of the first materials already cataloged and taking part in the synthesis process of the reference complex molecule and/or in the isotopic profile of the cleavage products of the reference complex molecule subjected to the same cleavage reactions.

The performance of the above steps permits applying such a process to no matter what complex molecule, without having proceeded to marking, particularly by enrichment in isotopes of the complex molecule to be analyzed.

According to a particular embodiment of the invention, starting with a selected isotope or isotopes, there is established the isotopic profile of at least a portion of the cleavage products at least by nuclear magnetic resonance (NMR) for measurement of the specific positional isotopic content and if desired by mass spectrometry of the isotopic ratios (MSIR) for the measurement of the overall isotopic content. It is to be noted that in the two preceding paragraphs, and in what follows, there is meant by isotopic profile the determination of the isotopic abundance at one or several sites of a molecule and not the measurement of the overall isotopic ratio of the whole molecule, which ratio is measured by isotopic mass spectrometry.

The invention resides in the following discovery by the inventors. Most of the organic molecules are obtained by means of a reaction sequence comprising a number of steps which can often be large when the complexity of the molecule increases. Each of these steps is characterized by kinetic isotopic effects (and/or thermodynamic effects) which give rise to specific isotopic fractionation, which is to say a selective isotopic marking, at the atomic sites (H, C, N, O . . . ) directly implicated in the reaction or located in the immediate vicinity of the reaction sites. It is thus possible to establish a chart of isotopic distribution of a complex molecule from isotopic profiles of the different steps used. The influence of the first materials and of the intermediate reagents adapted to be used, is also taken into account for establishing the isotopic profile of the molecule based on the individual profiles of a more or less great number of its constituent fragments.

Authentication takes place as follows:

On a sample of authentic product $P_0$ constituting the reference complex molecule, there is carried out a selective cleavage reaction of the molecule into at least two molecular sub-entities $P_{-1a}$ and $P_{-1b}$ that are lighter. The isotopic effects associated with this cleavage reaction are determined. The specific isotopic compositions of $P_{-1a}$ and $P_{-1b}$ are thus unequivocally connected to that of $P_0$. The specific isotopic parameters of the molecular sites of the fragments are measured by the SNIF-NMR method ($^2H$, $^{13}C$, $^{15}N$). A measurement of the overall isotopic content by isotopic mass spectrometry (MSIR) can also be carried out ($^{13}C$, $^2H$, $^{18}O$, $^{15}N$, $^{34}S$). The selection of the isotopes to be analyzed is done on the basis of reference data and spectroscopic characteristics of the fragment. In numerous cases, the SNIF-NMR measurement of $^2H$ will suffice for the characterization.

if the $P_{-1}$ fragments have a molecular size incompatible with a direct study by SNIF-NMR, the analysis sequence is restarted from $P_{-1(a\ or\ b)}$ to $P_{-2(a\ or\ b)}$ and so on until molecules generally used as primary or intermediate materials are obtained for the synthesis in organic industry.

The same study is then carried out, strictly under the same experimental conditions, on the complex molecule to be analyzed constituted for example by a product suspected of being a counterfeit or the result of an illicit patent copying. The comparison of the results obtained in the two studies permits establishing an irrefutable conclusion as to the conformity or non-conformity of the product and of the process used. These two steps on the basis of the process suffice to answer the question; conforming or non-conforming?

Setting aside the isotopic reaction effects, the isotopic parameters of the fragments Pi determined from the above authentication process are representative of relatively simple molecules which are frequently intermediates of the industrial synthesis of the medication or of the active product in question. These parameters therefore constitute reliable indicators of the basic elements used by the producing company and can be the object of a more rigorous investigation. In the case of non-conformity, they permit, with reference to the data on the molecules of modest size which may already be cataloged, characterizing the origin of the primary materials of the counterfeit product. One can thus conclude, not only that the product does not conform but that it has been prepared by such a catalog process or from such cataloged primary material. The analysis process described above thus permits if desired identifying the process used in the production of a non-authentic complex molecule.

Moreover, the producer who desires ultimately to authenticate his medication or active product, even if not protected by a patent, can introduce into his production system one or several synthetic intermediates, corresponding to one or several Pi fragments having an isotopic profile peculiar to themselves. This method creates in effect a marking of the product without the need to add an oxogenous marking element (as is the case during use of particular compound markers, metal traces, or products enriched in heavy isotopes such as $^{13}C$). A specific isotopic footprint can thus be conferred on the synthesis intermediate (molecule of medium size itself synthesized from petroleum derivatives or extracted from vegetable materials, etc.), either by selecting initial primary materials of a particular and constant isotopic content, or by acting on the isotopic effects associated with the reactions of preparation, extraction, purification of the intermediate corresponding to Pi. In the presence of kinetic isotopic effects, a variation of the yield for example can suffice to modify the fractionation and hence the isotopic profile of the synthetic intermediate. By applying the above analysis process to the complex molecule thus elaborated, there will be obtained one or more Pi fragments on which a unique isotopic profile has been conferred. The company will thus have isotopic parameters of one or several fragments of its product which will be unique to it. With this strategy, the product will not suffer the drawbacks which attach to the addition of exogenous elements or to the enrichment by isotopic marking. During inspection, the suspect product is studied under the conditions described above and the interpretation is carried out in the same way by comparison of the parameters of the fragments of the suspect product and of the reference product. In this case, the control can be simplified because it suffices to characterize the typical fragment or fragments. With this process, the producer has a practically incontestable method of characterizing his product and even of characterizing the batches of it because he need only change the source of a primary material or the conditions of synthesis of a fragment, to give to Pi a typical profile.

In short, in the scope of the analysis process described above, it is possible, during production of the complex reference molecule which can be subjected to the same cleavage reactions as the complex molecule to be analyzed, to select at least one primary material and/or intermediate product and/or conditions of synthesis, so as to give to at least one of the cleavage products of the reference complex molecule, called Pi, as above a unique character detectable during analysis without enrichment by isotopic markers and/or the addition of exogenous materials.

It is to be noted that the fragments or molecular sub-units are obtained by suitable chemical degradation processes such as are described in the example of use. The fragments are then separated and purified by various techniques, as for example liquid phase chromatography, gaseous phase chromatography or chromatography on silica gel, distillation, recrystallization, etc. The extraction purification protocols are first carefully standardized to avoid any uncontrolled isotopic fractionation.

An example of analysis of the process of production of a complex molecule is described below.

a) Description of the molecule to be analyzed:

By way of illustration of the process, let us consider the case of sildenafil citrate [VIAGRA, trademark] produced by Pfizer, belonging to the category of anti-anginal agents of the pyrazolopyrimidinone type.

Sildenafil cirate has the following chemical structure:
$C_{22}H_{30}N_6O_4S$, citrate M=474.6

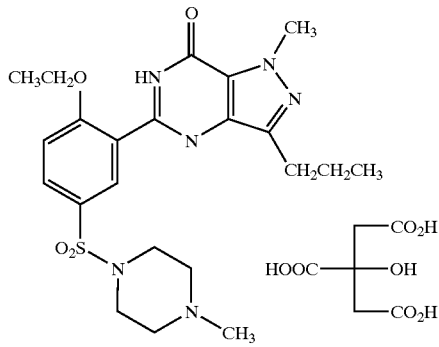

1-[4-ethoxy-3-(6,7-dihydro-1-methyl-7-oxo-3-propyl-1H-pyrazolo[4,3-d]pyrimidin-5-yl) phenylsulphonyl]-4-methylpiperazine citrate This molecule can be cleaved into several molecular fragments bearing a characteristic isotopic message, called "isotopic synthons"

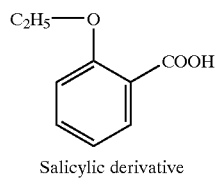

Salicylic derivative

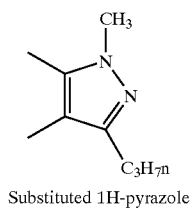

Substituted 1H-pyrazole

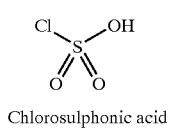

Chlorosulphonic acid methylpiperazine citric acid

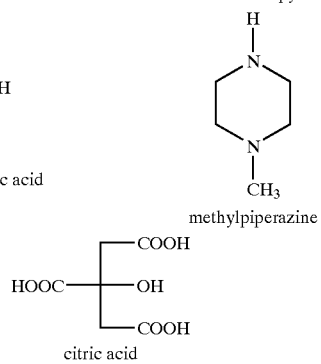

The reactions of isotopic retro filiation usable are thus as follows:

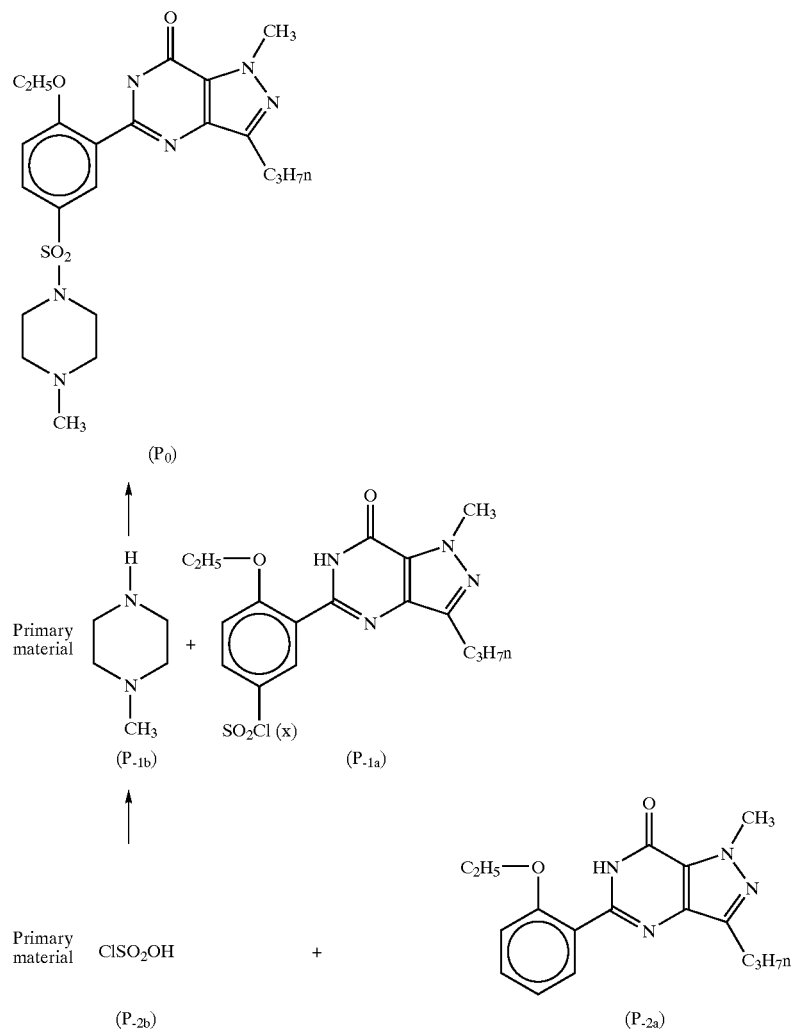

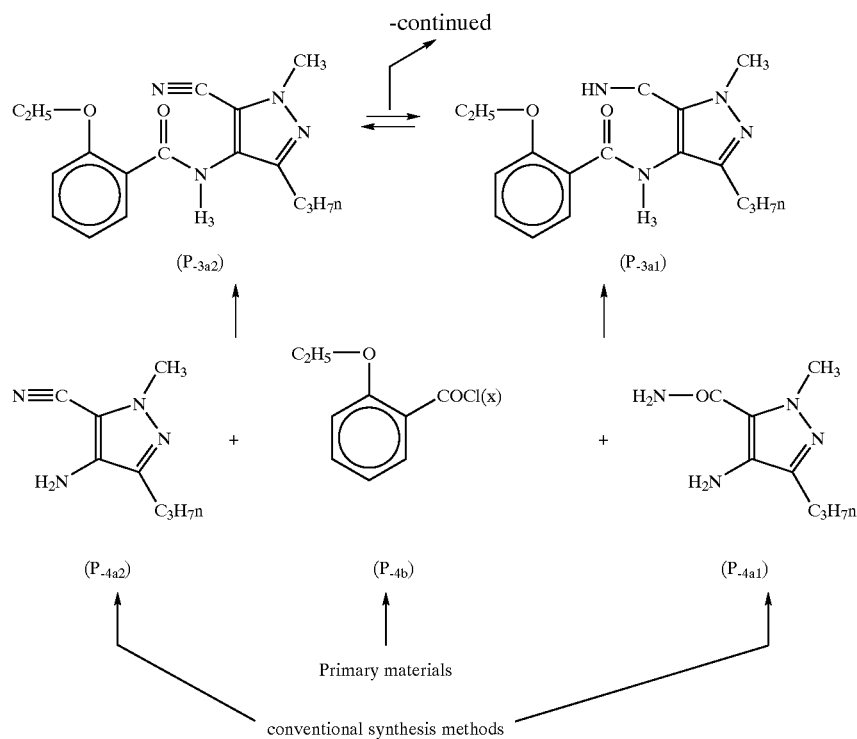

Occurrence and synthesis methods that can be used for primary materials $P_{-1b}$, $P_{-2b}$, $P_{-4a1}$, $P_{-4ab2}$ and $P_{-4b}$:

$P_{-1b}$: N-methylpiperazine $C_5H_{12}N_2$ M=100.16 CAS 109-01-3

$P_{-2b}$: chloro-sulfonic acid $SO_3HCl$ M=116.52 CAS 7790-94-5

$P_{-4a1}$ and $P_{-4a2}$: 1H-pyrazole, 1-methyl, 3-n propyl, 4-amino, 5-cyano or acetamido $C_8H_{12}N_4$ or $C_8H_{14}N_4O$ The synthesis of the substituted 1H-pyrazole ring can take place by means of a cyclization reaction in hydrazone from ethyl acylacetate and nucleophilic addition of the CN ion to the carbonyl of the cyclic hydrazone.

$P_{-4b}$: 2-ethoxy benzoic acid $C_9H_{10}O_3$ M=166.18 CAS 134-11-2

The primary materials P-1b, P-2b and P-4b are available commercially but it is interesting to prepare P-4a1 and P-4a2 by means of conventional syntheses of the 1H-pyrazole rings. These syntheses generally use substituted hydrazines of the $R_1NH$—$NH_2$ type and β-dicarboxyl compounds $R_3$—CO—$CH_2$—CO—$R_4$.

The isotopic contents of the usable primary materials are well documented in the literature.

The isotopic ratios R(i) are expressed in deviations δ(i) ‰ relative to an international reference R(ref) by means of the relationship:

$$\delta(i)=((R(i)/R(\text{ref}))-1)*10000$$

$^2H$ and $^{18}O$: V. SMOW (Vienna-Standard Mean Ocean Water)

$^{13}C$: V.PDB (Vienna-Pee Dee Belemnite)

$^{15}N$: atmospheric nitrogen $^{34}S$: CDT, specimen of Troilite extracted from Diablo Canyon (USA)

The benzine rings of fossil origin (petroleum) are characterized by values of δ $^2H$ comprised between −20 and −120‰ and the saturated side chains between 0 and −70. Measurements are carried out by NMR (SNIF-NMR) for the side chains and the overall content by Mass Spectrometry (MSIR). The overall contents in $^{13}C$ measured by MSIR are generally equal to −28.5‰ with a typical variation of the order of 2‰ and the isotopic contents of $^{13}C$ of the alkylated or functional side chains are measured by NMR. According to the synthesis process and the origin of the primary material of the side chains, the values δ $^{13}C$ can vary between −5 and −100‰ and thus offer an important characterization potential.

Nitrated molecules of synthetic origin have $^{13}C$ and $^{15}N$ values, measured by MSIR, which are relatively low and equal respectively to −30‰ (1.5) and −20‰ (10) but, in this latter case, the cyclization reactions of pyrazoles and xanthines lead to substantial impoverishment in heavy isotopes. At this level, it can be considered that the values of δ $^{15}N$ of the CN group or of the $CONH_2$ group reflect those of the primary materials because the introduction into the 1H-pyrazole pattern takes place without significant isotopic fractionation. The content in $^{15}N$ of the $NH_2$ group is all the lower relative to that of the primary material, the lower is the yield of the reaction.

Commercial chlorosulfonic acids are generally made from sulfuric acid whose $^{34}S$ content can vary between −25 and +25 ☐ according to the origin of the primary materal (native sulfur, pyrites) and of the process of production. However, once synthesized, the —$SO_2$— group is an excellent natural tracer and the content in $^{34}S$ is determined by MSIR.

Finally, it is interesting to note that the isotopic mapping of citric acid is very well defined and that the origin of the sildenafil citrate can be precisely determined by consideration of the isotopic distribution in the citrate fragment. Thus, the content of $^2H$ measured by NMR varies between −40 and −80‰ for biotechnological citric acids but the values $\delta^{13}C$ are equal respectively to −11‰ (1) or −25‰ (1) accordingly as the primary material is constituted by a C34 or C3 sugar. The natural citric acids extracted from fruits such as citrus, pineapple or red fruits have $\delta^2H$ values that are very near to 0‰ (25).

The range of variation which we have shown proves the feasibility of the process for production of a medication or active product. A great possibility of choice of isotopic values of one or several fragments is offered to the producing company desiring to carry out a "natural marking" of its product.

d) Characterization of the different reaction steps by establishment of an isotopic fractionation profile:

Step: level-4→level-3

No modification of the $^2H$ and $^{13}C$ contents of the benzene ring is achieved and, in the same way, the $\delta^{18}O$ value of the ethoxy group must not vary. The most significant variation is in the $NH_2$ function of P(-4a) which is subject to isotopic fractionation $^{15}N/^{14}N$ proportional to the kinetic effect α of the formation reaction of the amide bond and the corresponding fractionation is measured by MSIR.

It is to be noted however that the primary material P(-4b), 2-ethoxy benzoic acid, can be naturally and specifically marked without the addition of enriched molecules, in the following manner:

The $O-C_2H_5$ group is naturally marked with $^2H$, $^{13}C$ or $^{18}O$ from suitably chosen ethanol molecules. An ethanol synthesis has $^2H$ values equal respectively to −100 and −160‰ at the two $CH_3$ and $CH_2$ sites with $^{13}C$ contents of the order of −28 to −31‰ and $18_O$ contents equal to −5–10‰. Moreover, a natural ethanol could have $^2H$, $^{13}C$, or $^{18}O$ contents equal respectively to −200 and −400‰ ($^2H$), −11‰ ($^{13}C$) and +7/+10 ($^{18}O$). These two types of commercially available ethoxy groups without enriched addition, are easily introduced into the o-hydroxybenzoic acid molecule by means of conventional reactions to form the primary material P(-4b). The isotopic characteristics of this primary material, which become a typical fragment as described above, are present in the final molecule of sildenafil citrate.

Step: level-3→level -2

In the course of this step, there can be observed by MSIR characteristic variations of the $\delta^{15}N$ contents of the nitrogen atoms of the pyrimidinone ring The $\delta^2H$ and $\delta^{18}O$ values of the NH and C=O cites are not usable because they depend on chemical exchanges with the medium.

Step: level-2→level-1

In the course of this reaction step, the benzine ring is sulfonated by means of a reaction of the electrophilic substitution type at low temperature. The $^{34}S$ content, measured by MSIR, can be very slightly modified, but this modification is the less as the sulfonation yield is higher. No modification is expected for the other isotopomers of P(-1a).

Step: level-1→level 0

The attachment of the piperazine ring of (P-1b) to the sulfonyl group of P(-1a) can give rise to a slight decrease in $^{15}N$ of the piperazine fragment fixed to the sildanefil sulfate. This decrease, which is measured by MSIR, can if desired be characterized in the cleavage product of sildanefil citrate. The other isotopic contents are not changed in the course of this step.

What is claimed is:

1. A process for the analysis of a sample of a complex molecule relative to a reference batch of the same complex molecule so as to determine their degree of similarity and/or the nature of their process of production, comprising:

cleaving the complex molecule into at least two molecular sub-entities, in that, if necessary, at least one of the cleavage products is cleaved into at least two new molecular sub-entities and in that this cleavage operation is repeatable on the molecular sub-entities until analyzable and isolable molecular sub-entities are obtained, in that there is determined, as a function of the atomic sites of the cleavage products in question, by generally chemical cleavage reactions, the isotope or isotopes to be studied, in that there is established, for at least a portion of the cleavage products, their isotopic profile at least by nuclear magnetic resonance NMR for the measurement of the specific positional isotopic content and in that the isotopic profile of the cleavage products is compared to the isotopic profile of primary materials already cataloged and taking part in the synthesis process of the reference complex molecule and/or in the isotopic profile of the cleavage products of the reference complex molecule subjected to the same cleavage reactions.

2. A process according to claim 1, wherein, starting from a selected isotope or isotopes, there is established the isotopic profile of at least a portion of the cleavage products at least by nuclear magnetic resonance NMR for the measurement of the specific positional isotopic content and if desired by mass spectrometry, of the isotopic ratios for measuring the overall isotopic content.

3. The process according to claim 1, wherein, during production of the complex reference molecule before being subjected to the same cleavage reactions as the complex molecule to be analyzed, there is selected at least one primary material and/or an intermediate product and/or material synthesis conditions to give to at least one of the cleavage products of the reference complex molecule a unique characteristic detectable during analysis without enrichment by isotopic marking and/or the addition of exogenous elements.

4. A process for the analysis of a sample of a complex molecule relative to a reference batch of the same complex molecule, comprising:

cleaving said sample complex molecule so that analyzable and isolable molecular sub-entities are obtained;

determining an isotope or isotopes of the cleavage product by Nuclear Magnetic Resonance (NMR);

comparing the isotopic profile of the cleavage products to the isotopic profiles of primary materials already cataloged and taking part in the synthesis process of the complex molecule of the reference batch and/or comparing the isotopic profile of the cleavage products of the sample to the isotopic profile of the reference complex molecule subjected to the same cleavage reaction; and analyzing results of the comparison to determine the degree of similarity of the complex molecule of the sample relative to the complex molecule of the reference batch.

5. A process for the analysis of a sample of a complex molecule relative to a reference batch of the same complex molecule, comprising:

cleaving said sample complex molecule so that analyzable and isolable molecular sub-entities are obtained;

determining an isotope or isotopes of the cleavage product by Nuclear Magnetic Resonance (NMR);

comparing the isotopic profile of the cleavage products to the isotopic profiles of primary materials already cataloged and taking part in the synthesis process of the complex molecule of the reference batch and/or comparing the isotopic profile of the cleavage products of the sample to the isotopic profile of the reference complex molecule subjected to the same cleavage reaction; and analyzing results of the comparison to determine how the sample complex molecule was synthesized.

* * * * *